US011862520B2

United States Patent
Sundar et al.

(10) Patent No.: US 11,862,520 B2
(45) Date of Patent: Jan. 2, 2024

(54) SYSTEMS AND METHODS FOR PREDICTING FILM THICKNESS OF INDIVIDUAL LAYERS USING VIRTUAL METROLOGY

(71) Applicant: Applied Materials, Inc., Santa Clara, CA (US)

(72) Inventors: Bharath Ram Sundar, Chennai (IN); Raman K. Nurani, Chennai (IN); Utkarsha Avinash Dhanwate, Amravati (IN); Ramakrishnan S. Hariharan, Trichy (IN); Suresh Bharatharajan Kudallur, Chennai (IN); Vishwath Ram Amarnath, Chennai (IN)

(73) Assignee: Applied Materials, Inc., Santa Clara, CA (US)

( * ) Notice: Subject to any disclaimer, the term of this patent is extended or adjusted under 35 U.S.C. 154(b) by 507 days.

(21) Appl. No.: 17/166,288

(22) Filed: Feb. 3, 2021

(65) Prior Publication Data
US 2022/0246481 A1 Aug. 4, 2022

(51) Int. Cl.
*H01L 21/66* (2006.01)
*G01N 23/2251* (2018.01)
(Continued)

(52) U.S. Cl.
CPC ............. *H01L 22/12* (2013.01); *G01N 23/04* (2013.01); *G01N 23/2251* (2013.01);
(Continued)

(58) Field of Classification Search
CPC ......... H01L 22/12; H01L 22/26; G06N 20/00; G06F 18/214; G01N 23/04; G01N 23/2251
See application file for complete search history.

(56) References Cited

U.S. PATENT DOCUMENTS

2020/0193290 A1   6/2020  Cho et al.
2022/0374572 A1*  11/2022 Sawlani ................. G06N 20/00

FOREIGN PATENT DOCUMENTS

KR        100982306 B1    9/2010
KR      20130124904 A    11/2013
(Continued)

OTHER PUBLICATIONS

PCT Notification of Transmittal Of The International Search Report And The Written Opinion Of The International Searching Authority for PCT Application No. PCT/US2022/013183, dated May 12, 2022, 9 pages.

*Primary Examiner* — Feifei Yeung Lopez
(74) *Attorney, Agent, or Firm* — Lowenstein Sandler LLP

(57) ABSTRACT

A method includes obtaining sensor data associated with a deposition process performed in a process chamber to deposit a film stack on a surface of a substrate, wherein the film stack comprises a plurality of layers of a first material and a plurality of layers of a second material. The method further includes obtaining metrology data associated with the film stack. The method further includes training a first machine-learning model based on the sensor data and the metrology data, wherein the first machine-learning model is trained to generate predictive metrology data associated with layers of the first material. The method further includes training a second machine-learning model based on the sensor data and the metrology data, wherein the second machine-learning model is trained to generate predictive metrology data associated with layers of the second material.

20 Claims, 6 Drawing Sheets

(51) Int. Cl.
*G01N 23/04* (2018.01)
*G06N 20/00* (2019.01)
*G06F 18/214* (2023.01)

(52) U.S. Cl.
CPC ........... *G06F 18/214* (2023.01); *G06N 20/00* (2019.01); *H01L 22/26* (2013.01)

(56) References Cited

FOREIGN PATENT DOCUMENTS

| | | | |
|---|---|---|---|
| WO | 2014081902 | A1 | 5/2014 |
| WO | 2016010821 | A1 | 1/2016 |

* cited by examiner

SYSTEMS AND METHODS FOR PREDICTING FILM THICKNESS OF INDIVIDUAL LAYERS USING VIRTUAL METROLOGY

TECHNICAL FIELD

The present disclosure relates to electrical components, and, more particularly, to predicting film thickness of individual layers using virtual metrology.

BACKGROUND

Products may be produced by performing one or more manufacturing processes using manufacturing equipment. For example, semiconductor manufacturing equipment may be used to produce semiconductor devices (e.g., substrates, wafers, etc.) via semiconductor manufacturing processes. The manufacturing equipment can deposit multiple layers of film on the surface of the substrate and can perform an etch process to form the intricate pattern in the deposited film. For example, the manufacturing equipment may perform a chemical vapor deposition (CVD) process to deposit alternative oxide and nitride layers on the substrate. Sensors may be used to determine manufacturing parameters of the manufacturing equipment during the manufacturing processes and metrology equipment may be used to determine property data of the products that were produced by the manufacturing equipment, such as the overall thickness of the layers on the substrate. Generally, the metrology equipment cannot measure the thickness of individual layers on the substrate (e.g., the thickness of each oxide and each nitride layer) until the manufacturing process is completed, and not without using a destructive testing process such as a Transmission Electron Microscope (TEM) analysis. As such, it may be difficult to detect excursions on individual film layers during manufacturing and adjust the deposition rate.

SUMMARY

The following is a simplified summary of the disclosure in order to provide a basic understanding of some aspects of the disclosure. This summary is not an extensive overview of the disclosure. It is intended to neither identify key or critical elements of the disclosure, nor delineate any scope of the particular implementations of the disclosure or any scope of the claims. Its sole purpose is to present some concepts of the disclosure in a simplified form as a prelude to the more detailed description that is presented later.

In an aspect of the disclosure, a method includes obtaining, by a processor, sensor data associated with a deposition process performed in a process chamber to deposit a film stack on a surface of a substrate, wherein the film stack comprises a plurality of layers of a first material and a plurality of layers of a second material. The method further includes obtaining metrology data associated with the film stack. The method further includes training a first machine-learning model based on the sensor data and the metrology data, wherein the first machine-learning model is trained to generate predictive metrology data associated with layers of the first material. The method further includes training a second machine-learning model based on the sensor data and the metrology data, wherein the second machine-learning model is trained to generate predictive metrology data associated with layers of the second material.

In another aspect of the disclosure, a system includes a memory; and a processing device, coupled to the memory, to obtain sensor data associated with a deposition process performed in a process chamber to deposit a film stack on a surface of a substrate, wherein the film stack comprises a plurality of layers of a first material and a plurality of layers of a second material. The processing device is further to obtain metrology data associated with the film stack. The processing device is further to train a first machine-learning model based on the sensor data and the metrology data, wherein the first machine-learning model is trained to generate predictive metrology data associated with layers of the first material. The processing device is further to train a second machine-learning model based on the sensor data and the metrology data, wherein the second machine-learning model is trained to generate predictive metrology data associated with layers of the second material.

In another aspect of the disclosure, a non-transitory machine-readable storage medium storing instructions which, when executed cause a processing device to perform operations including obtaining, by a processor, sensor data associated with a deposition process performed in a process chamber to deposit a film stack on a surface of a substrate, wherein the film stack comprises a plurality of layers of a first material and a plurality of layers of a second material. The operations further include obtaining metrology data associated with the film stack. The operations further include training a first machine-learning model based on the sensor data and the metrology data, wherein the first machine-learning model is trained to generate predictive metrology data associated with layers of the first material. The operations further include training a second machine-learning model based on the sensor data and the metrology data, wherein the second machine-learning model is trained to generate predictive metrology data associated with layers of the second material.

In another aspect of the disclosure, a method includes obtaining a plurality of sensor values associated with a deposition process performed in a process chamber to deposit layers of film on a surface of a substrate. The method further includes applying a first machine-learning model to a first subset of the plurality of sensor values, the machine-learning model trained based on historical sensor data and metrology data associated with layers of a first material. The method further includes applying a second machine-learning model to a second subset of the plurality of sensor values, the machine-learning model trained based on the historical sensor data and metrology data associated with layers of a second material. The method further includes obtaining a first output of the first machine-learning model, the first output identifying first predictive metrology data for layers of the first material of the film. The method further includes obtaining a second output of the second machine-learning model, the second output identifying second predictive metrology data for layers of the second material of the film

BRIEF DESCRIPTION OF THE DRAWINGS

The present disclosure is illustrated by way of example, and not by way of limitation in the figures of the accompanying drawings.

DETAILED DESCRIPTION

Figure 1:
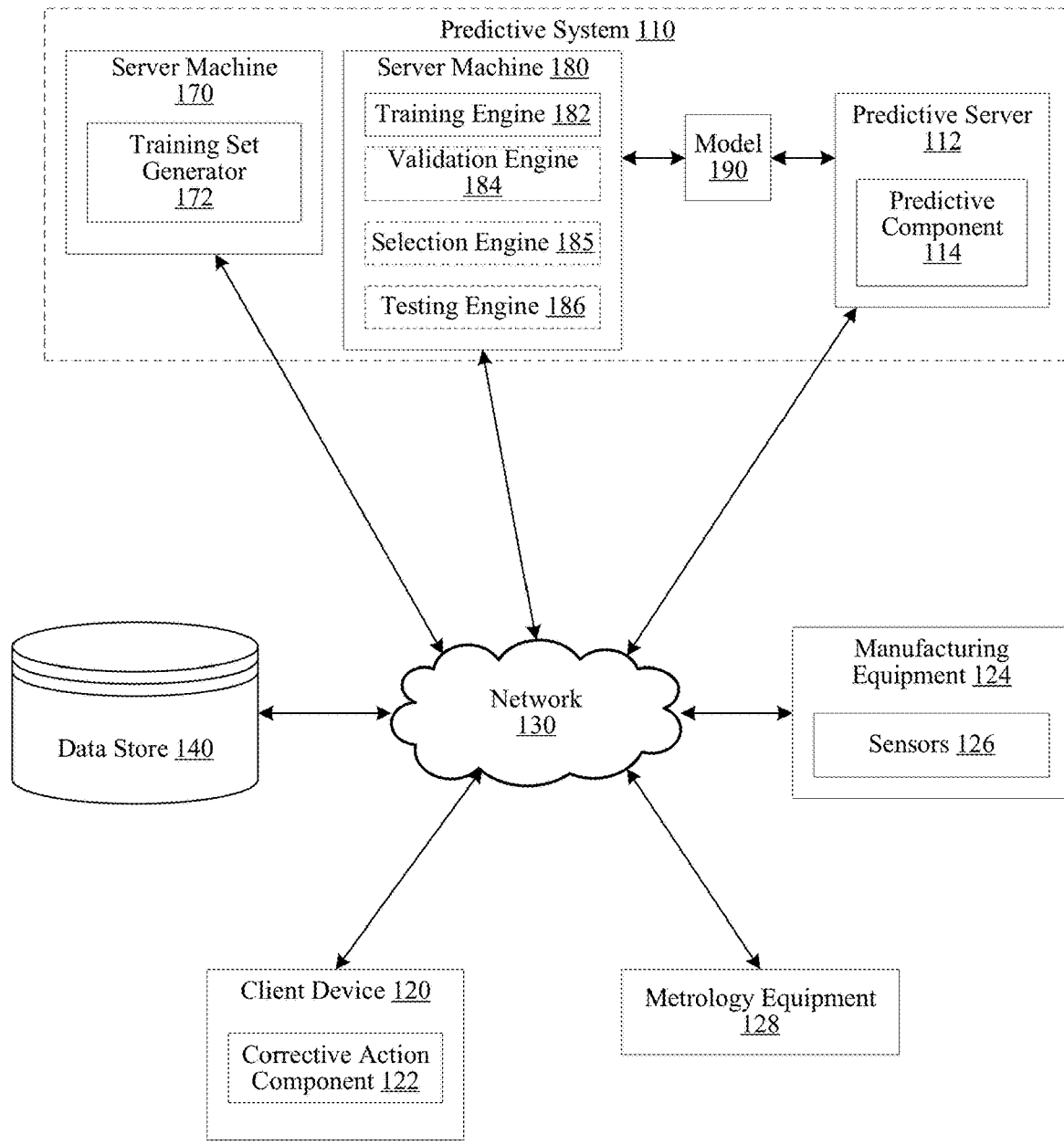
FIG. 1 is a block diagram illustrating an exemplary system architecture, according to certain embodiments.

Described herein are technologies directed to systems and methods for predicting film thickness of individual layers using virtual metrology. A film can be deposited on a surface of a substrate during a deposition process performed at a process chamber of a manufacturing system. For example, in a chemical vapor deposition (CVD) process, the substrate is exposed to one or more precursors, which react on the substrate surface to produce the desired deposit. The film can include one or more layers of materials (hereafter "film stack") that are formed during the deposition process, and each layer can include a particular thickness gradient (e.g., changes in the thickness along a layer of the deposited film). For example, a first layer can be formed directly on the surface of the substrate (referred to as a proximal layer or proximal end of the film) and have a first thickness. After the first layer is formed on the surface of the substrate, a second layer having a second thickness can be formed on the first layer. This process continues until the deposition process is completed and a final layer is formed for the film (referred to as the distal layer or distal end of the film). The film stack can include alternating layers of different materials. For example, a film stack can include alternating layers of oxide and nitride layers (oxide-nitride-oxide-nitride stack or ONON stack), alternating oxide and polysilicon layers (oxide-polysilicon-oxide-polysilicon stack or OPOP stack), and so forth.

In some existing systems, metrology measurements are performed on substrates of a batch to generate metrology data, such as thickness data. For example, metrology equipment can analyze a substrate to determine the thickness of each layer in the film stack. Using the metrology data, the systems can perform quality control by adjusting a deposition rate of one or more layers to decrease defects and improve layer uniformity. This is important because a defect or small variation in layer thickness can result in a large deviation at the top of a film stack. However, existing systems cannot measure the thickness of individual layers on the substrate until the film stack is completed, and not without using destructive testing processes to obtain metrology data for each layer in the film stack.

Aspects and implementations of the present disclosure address these and other shortcoming of existing technology by training a machine-learning model capable of generating predictive metrology data for each layer in a film stack. In some embodiments, the machine-learning model can be generated based on training data, which includes data from one or more sensors mapped to film thickness data. The film thickness data can include measured thickness values obtained from measuring individual layers of material produced by the manufacturing equipment or measured thickness values obtained from measuring film stacks produced by the manufacturing equipment. In some embodiments, the film thickness data can be generated using reflectometry techniques, ellipsometry techniques, a TEM analysis, or any other measurement techniques. In some embodiments, the machine-learning model can be calibrated using measured metrology data.

In some embodiments, the system of the present disclosure can generate different trained machine-learning models for each type of material used in a film stack. For example, the present system can train a first machine-learning model to generate predictive metrology data used to predict the thickness of each oxide layer in an ONON stack generated by a process chamber, and train a second machine-learning model to generate predictive metrology data used to predict the thickness of each nitride layer in the ONON stack. The predictive metrology data can include a contour map (e.g., a vector map) including a set of spatial measurements (e.g., a set of vectors), each indicating a thickness of a particular location of a plurality of locations on each layer.

In some embodiments, the predictive metrology data can be compared to actual (measured) metrology data of the substrate, which can be used to update or calibrate the machine-learning models. In one example, the trained machine-learning model can be calibrated based on the predictive metrology data and the measured mass of the film stack. In another example, the trained machine-learning model can be calibrated based on the predictive metrology data and the measured thickness of the film stack.

Aspects of the present disclosure result in technological advantages of significant reduction in time required to achieve optimal settings during manufacturing of substrates, as well as improvements in energy consumption, and so forth. The disclosed technology results in reduced time requirements and eliminates using destructive techniques to measure individual layer thickness in film stacks by training one or more machine-learning models which can be used to obtain predictive data, detect excursions early during manufacturing of a film stack, and cause performance of corrective actions based on the predictive data. The disclosed technology can result in predicting metrology data for layers in real-time or near real-time to avoid inconsistent and abnormal products, unscheduled user time, and unnecessary metrology measurements.

FIG. 1 depicts an illustrative computer system architecture 100, according to aspects of the present disclosure. In some embodiments, computer system architecture 100 can be included as part of a manufacturing system for processing substrates, such as manufacturing system 300 of FIG. 3. Computer system architecture 100 includes a client device 120, manufacturing equipment 124, metrology equipment 128, a predictive server 112 (e.g., to generate predictive data, to provide model adaptation, to use a knowledge base, etc.), and a data store 140. The predictive server 112 can be part of a predictive system 110. The predictive system 110 can further include server machines 170 and 180. The manufacturing equipment 124 can include sensors 126 configured to capture data for a substrate being processed at the manufacturing system. In some embodiments, the manufacturing equipment 124 and sensors 126 can be part of a sensor system that includes a sensor server (e.g., field service server (FSS) at a manufacturing facility) and sensor identifier reader (e.g., front opening unified pod (FOUP) radio frequency identification (RFID) reader for sensor system). In some embodiments, metrology equipment 128 can be part of a metrology system that includes a metrology server (e.g., a metrology database, metrology folders, etc.) and metrology identifier reader (e.g., FOUP RFID reader for metrology system).

Manufacturing equipment 124 can produce products, such as electronic devices, following a recipe or performing runs over a period of time. Manufacturing equipment 124 can include a process chamber, such as process chamber 400 described with respect to FIG. 4. Manufacturing equipment 124 can perform a process for a substrate (e.g., a wafer, etc.) at the process chamber. Examples of substrate processes include a deposition process to deposit one or more layers of film on a surface of the substrate, an etch process to form a pattern on the surface of the substrate, etc. Manufacturing equipment 124 can perform each process according to a process recipe. A process recipe defines a particular set of operations to be performed for the substrate during the process and can include one or more settings associated with each operation. For example, a deposition process recipe can include a temperature setting for the process chamber, a pressure setting for the process chamber, a flow rate setting for a precursor for a material included in the film deposited on the substrate surface, etc.

In some embodiments, manufacturing equipment 124 can include sensors 126 that are configured to generate data associated with a substrate processed at manufacturing system 100. For example, a process chamber can include one or more sensors configured to generate spectral or non-spectral data associated with the substrate before, during, and/or after a process (e.g., a deposition process) is performed for the substrate. In some embodiments, spectral data generated by sensors 126 can indicate a concentration of one or more materials deposited on a surface of a substrate. Sensors 126 configured to generate spectral data associated with a substrate can include reflectometry sensors, ellipsometry sensors, thermal spectra sensors, capacitive sensors, and so forth. Sensors 126 configured to generate non-spectral data associated with a substrate can include temperature sensors, pressure sensors, flow rate sensors, voltage sensors, etc. Further details regarding manufacturing equipment 124 are provided with respect to FIG. 3 and FIG. 4.

In some embodiments, sensors 126 can provide sensor data (e.g., sensor values, features, trace data) associated with manufacturing equipment 124 (e.g., associated with producing, by manufacturing equipment 124, corresponding products, such as wafers). The manufacturing equipment 124 may produce products following a recipe or performing runs over a period of time. Sensor data received over a period of time (e.g., corresponding to at least part of a recipe or run) may be referred to as trace data (e.g., historical trace data, current trace data, etc.) received from different sensors 126 over time. Sensor data can include a value of one or more of temperature (e.g., heater temperature), spacing (SP), pressure, high frequency radio frequency (HFRF), voltage of electrostatic chuck (ESC), electrical current, material flow, power, voltage, etc. Sensor data can be associated with or indicative of manufacturing parameters such as hardware parameters, such as settings or components (e.g., size, type, etc.) of the manufacturing equipment 124, or process parameters of the manufacturing equipment 124. The sensor data can be provided while the manufacturing equipment 124 is performing manufacturing processes (e.g., equipment readings when processing products). The sensor data can be different for each substrate.

Metrology equipment 128 can provide metrology data associated with substrates processed by manufacturing equipment 124. The metrology data can include a value of film property data (e.g., wafer spatial film properties), dimensions (e.g., thickness, height, etc.), dielectric constant, dopant concentration, density, defects, etc. In some embodiments, the metrology data can further include a value of one or more surface profile property data (e.g., an etch rate, an etch rate uniformity, a critical dimension of one or more features included on a surface of the substrate, a critical dimension uniformity across the surface of the substrate, an edge placement error, etc.). The metrology data can be of a finished or semi-finished product. The metrology data can be different for each substrate. Metrology data can be generated using, for example, reflectometry techniques, ellipsometry techniques, TEM techniques, and so forth.

In some embodiments, metrology equipment 128 can be included as part of the manufacturing equipment 124. For example, metrology equipment 128 can be included inside of or coupled to a process chamber and configured to generate metrology data for a substrate before, during, and/or after a process (e.g., a deposition process, an etch process, etc.) while the substrate remains in the process chamber. In such instances, metrology equipment 128 can be referred to as in-situ metrology equipment. In another example, metrology equipment 128 can be coupled to another station of manufacturing equipment 124. For example, metrology equipment can be coupled to a transfer chamber, such as transfer chamber 310 of FIG. 3, a load lock, such as load lock 320, or a factory interface, such as factory interface 306. In such instances, metrology equipment 128 can be referred to as integrated metrology equipment. In other or similar embodiments, metrology equipment 128 is not coupled to a station of manufacturing equipment 124. In such instances, metrology equipment 128 can be referred to as inline metrology equipment or external metrology equipment. In some embodiments, integrated metrology equipment and/or inline metrology equipment are configured to generate metrology data for a substrate before and/or after a process.

The client device 120 my include a computing device such as personal computers (PCs), laptops, mobile phones, smart phones, tablet computers, netbook computers, network connected televisions ("smart TVs"), network-connected media players (e.g., Blu-ray player), a set-top box, over-the-top (OTT) streaming devices, operator boxes, etc. In some embodiments, the metrology data can be received from the client device 120. Client device 120 can display a graphical user interface (GUI), where the GUI enables the user to provide, as input, metrology measurement values for substrates processed at the manufacturing system. The client device 120 can include a corrective action component 122. Corrective action component 122 can receive user input (e.g., via a Graphical User Interface (GUI) displayed via the client device 120) of an indication associated with manufacturing equipment 124. In some embodiments, the corrective action component 122 transmits the indication to the predictive system 110, receives output (e.g., predictive data) from the predictive system 110, determines a corrective action based on the output, and causes the corrective action to be implemented. In some embodiments, the corrective action component 122 receives an indication of a corrective action from the predictive system 110 and causes the corrective action to be implemented. Each client device 120 may include an operating system that allows users to one or more of generate, view, or edit data (e.g., indication associated with manufacturing equipment 124, corrective actions associated with manufacturing equipment 124, etc.)

Data store 140 can be a memory (e.g., random access memory), a drive (e.g., a hard drive, a flash drive), a database system, or another type of component or device capable of storing data. Data store 140 can include multiple storage components (e.g., multiple drives or multiple databases) that can span multiple computing devices (e.g., multiple server computers). The data store 140 can store data associated with processing a substrate at manufacturing equipment 124. For example, data store 140 can store data collected by sensors 126 at manufacturing equipment 124 before, during, or after a substrate process (referred to as process data). Process data can refer to historical process data (e.g., process data generated for a prior substrate processed at the manufacturing system) and/or current process data (e.g., process data generated for a current substrate processed at the manufacturing system). Data store can also store spectral data or non-spectral data associated with a portion of a substrate processed at manufacturing equipment 124. Spectral data can include historical spectral data and/or current spectral data.

In some embodiments, data store 140 can also store film thickness data associated with one or more layers deposited on a surface of a substrate. Film thickness data refers to a particular thickness gradient of the deposited film (e.g., changes in the thickness along a layer of deposited film). In some embodiments, film thickness data can include a thickness value of a film stack (e.g., multiple layers of one or more materials) deposited on a surface of a substrate (e.g., as determined by metrology inspection or as determined by prediction). For example, the film thickness data can include a thickness value(s) of an ONON stack, an OPOP stack, an aggregated stack (e.g., an aggregated oxide stack, an aggregated nitride stack, an aggregated polysilicon stack etc.), or any other film stack generated by the manufacturing equipment 124. An aggregated stack can include thickness data associated with layers of a single material from a film stack having multiple layers of different materials. For example, from an ONON stack, an aggregated oxide stack can include thickness data from only the oxide layers, and an aggregated nitride stack can include thickness data from only the nitride layers. In some embodiments, one or more film stacks can be generated in a test production run for training machine-learning model 190 (e.g., for use by the training set generator 172 and/or training engine 182), which will be explained in greater detail below.

In some embodiments, film thickness data can include thickness values of individual layers deposited on a surface of a substrate (e.g., as determined by metrology inspection or as determined by prediction). For example, the film thickness data can include a thickness value(s) one or more layers of an ONON stack, one or more layers of an OPOP stack, one or more layers of an aggregated oxide stack, one or more layers of an aggregated nitride stack, one or more layers of an aggregated polysilicon stack, or any other layer(s) generated by the manufacturing equipment 124. In some embodiments, one or more layers can be generated in a test production run for training machine-learning model 190.

In some embodiments, film thickness data can be provided by a user (e.g., an operator) of the manufacturing system (e.g., via client device 120). In other or similar embodiments, film thickness data can be determined by a processing device of the manufacturing system, (e.g., system controller 328 of FIG. 3) based on sensor data and/or metrology data stored at the data store 140. Film thickness data can refer to historical thickness data (e.g., film thickness data for a prior film deposited on a prior substrate) or current thickness data (e.g., film thickness data for a current film deposited on a current substrate).

In some embodiments, film thickness data can also include data associated with a target thickness for a film to be deposited on a surface of a substrate. For example, a user of the operating system (e.g., an operator) can provide data associated with a target film thickness via client device 120. The data associated with the target film thickness can include at least of a target thickness of the film to be deposited on the surface of the substrate, a target initial thickness of a particular material of the film (e.g., a thickness of the particular material at a proximal layer of the film, and a target final thickness of the particular material of the film (e.g., a thickness of the particular material at the distal layer of the film). In some embodiments, the data associated with the target thickness can also include an indication of a target rate of change (e.g., linear, non-linear, etc.) of the thickness gradient for the particular material within the layers between the proximal and distal layers of the film.

The data store 140 can also store contextual data associated with one or more substrates processed at the manufacturing system. Contextual data can include a recipe name, recipe step number, preventive maintenance indicator, operator, etc. Contextual data can refer to historical contextual data (e.g., contextual data associated with a prior process performed for a prior substrate) and/or current process data (e.g., contextual data associated with current process or a future process to be performed for a prior substrate). In some embodiments, contextual data can also include an indication of one or more settings associated with a particular process. For example, contextual data for a deposition process can include a temperature setting for a process chamber, a pressure setting for a process chamber, a flow rate setting for a precursor for a material of a film deposited on a substrate, etc.

In some embodiments, data store 140 can be configured to store data that is not accessible to a user of the manufacturing system. For example, process data, spectral data, contextual data, etc. obtained for a substrate being processed at the manufacturing system is not accessible to a user (e.g., an operator) of the manufacturing system. In some embodiments, all data stored at data store 140 can be inaccessible by the user of the manufacturing system. In other or similar embodiments, a portion of data stored at data store 140 can be inaccessible by the user while another portion of data stored at data store 140 can be accessible by the user. In some embodiments, one or more portions of data stored at data store 140 can be encrypted using an encryption mechanism that is unknown to the user (e.g., data is encrypted using a private encryption key). In other or similar embodiments, data store 140 can include multiple data stores where data that is inaccessible to the user is stored in one or more first data stores and data that is accessible to the user is stored in one or more second data stores.

In some embodiments, predictive system 110 includes predictive server 112, server machine 170 and server machine 180. The predictive server 112, server machine 170, and server machine 180 may each include one or more computing devices such as a rackmount server, a router computer, a server computer, a personal computer, a mainframe computer, a laptop computer, a tablet computer, a desktop computer, Graphics Processing Unit (GPU), accelerator Application-Specific Integrated Circuit (ASIC) (e.g., Tensor Processing Unit (TPU)), etc.

Server machine 170 includes a training set generator 172 that is capable of generating training data sets (e.g., a set of data inputs and a set of target outputs) to train, validate, and/or test a machine-learning model 190. Machine-learning model 190 can be any algorithmic model capable of learning from data. Some operations of data set generator 172 is described in detail below with respect to FIG. 2. In some embodiments, the data set generator 172 can partition the training data into a training set, a validating set, and a testing set. In some embodiments, the predictive system 110 generates multiple sets of training data.

Server machine 180 can include a training engine 182, a validation engine 184, a selection engine 185, and/or a testing engine 186. An engine can refer to hardware (e.g., circuitry, dedicated logic, programmable logic, microcode, processing device, etc.), software (such as instructions run on a processing device, a general purpose computer system, or a dedicated machine), firmware, microcode, or a combination thereof. Training engine 182 can be capable of training one or more machine-learning models 190. Machine-learning model 190 can refer to the model artifact that is created by the training engine 182 using the training data (also referred to herein as a training set) that includes training inputs and corresponding target outputs (correct answers for respective training inputs). The training engine 182 can find patterns in the training data that map the training input to the target output (the answer to be predicted), and provide the machine-learning model 190 that captures these patterns. The machine-learning model 190 can use one or more of a statistical modelling, support vector machine (SVM), Radial Basis Function (RBF), clustering, supervised machine-learning, semi-supervised machine-learning, unsupervised machine-learning, k-nearest neighbor algorithm (k-NN), linear regression, random forest, neural network (e.g., artificial neural network), etc.

The validation engine 184 can be capable of validating machine-learning model 190 using a corresponding set of features of a validation set from training set generator 172. The validation engine 184 can determine an accuracy of machine-learning model 190 based on the corresponding sets of features of the validation set. The validation engine 184 can discard a trained machine-learning model 190 that has an accuracy that does not meet a threshold accuracy. In some embodiments, the selection engine 185 can be capable of selecting a trained machine-learning model 190 that has an accuracy that meets a threshold accuracy. In some embodiments, the selection engine 185 can be capable of selecting the trained machine-learning model 190 that has the highest accuracy of the trained machine-learning models 190.

The testing engine 186 can be capable of testing a trained machine-learning model 190 using a corresponding set of features of a testing set from data set generator 172. For example, a first trained machine-learning model 190 that was trained using a first set of features of the training set can be tested using the first set of features of the testing set. The testing engine 186 can determine a trained machine-learning model 190 that has the highest accuracy of all of the trained machine-learning models based on the testing sets.

As described in detail below, predictive server 112 includes a predictive component 114 that is capable of providing data associated with film thickness data for one or more layers of film deposited on a surface of a substrate during a deposition process for the substrate, and running trained machine-learning model 190 on the input to obtain one or more outputs. The predictive server 112 can further provide metrology predictions of each layer of a film stack produced during deposition process. This will be explained in further detail below.

The client device 120, manufacturing equipment 124, sensors 126, metrology equipment 128, predictive server 112, data store 140, server machine 170, and server machine 180 can be coupled to each other via a network 130. In some embodiments, network 130 is a public network that provides client device 120 with access to predictive server 112, data store 140, and other publically available computing devices. In some embodiments, network 130 is a private network that provides client device 120 access to manufacturing equipment 124, metrology equipment 128, data store 140, and other privately available computing devices. Network 130 can include one or more wide area networks (WANs), local area networks (LANs), wired networks (e.g., Ethernet network), wireless networks (e.g., an 802.11 network or a Wi-Fi network), cellular networks (e.g., a Long Term Evolution (LTE) network), routers, hubs, switches, server computers, cloud computing networks, and/or a combination thereof.

It should be noted that in some other implementations, the functions of server machines 170 and 180, as well as predictive server 112, can be provided by a fewer number of machines. For example, in some embodiments, server machines 170 and 180 can be integrated into a single machine, while in some other or similar embodiments, server machines 170 and 180, as well as predictive server 112, can be integrated into a single machine.

In general, functions described in one implementation as being performed by server machine 170, server machine 180, and/or predictive server 112 can also be performed on client device 120. In addition, the functionality attributed to a particular component can be performed by different or multiple components operating together.

In embodiments, a "user" can be represented as a single individual. However, other embodiments of the disclosure encompass a "user" being an entity controlled by a plurality of users and/or an automated source. For example, a set of individual users federated as a group of administrators can be considered a "user."

Figure 2:
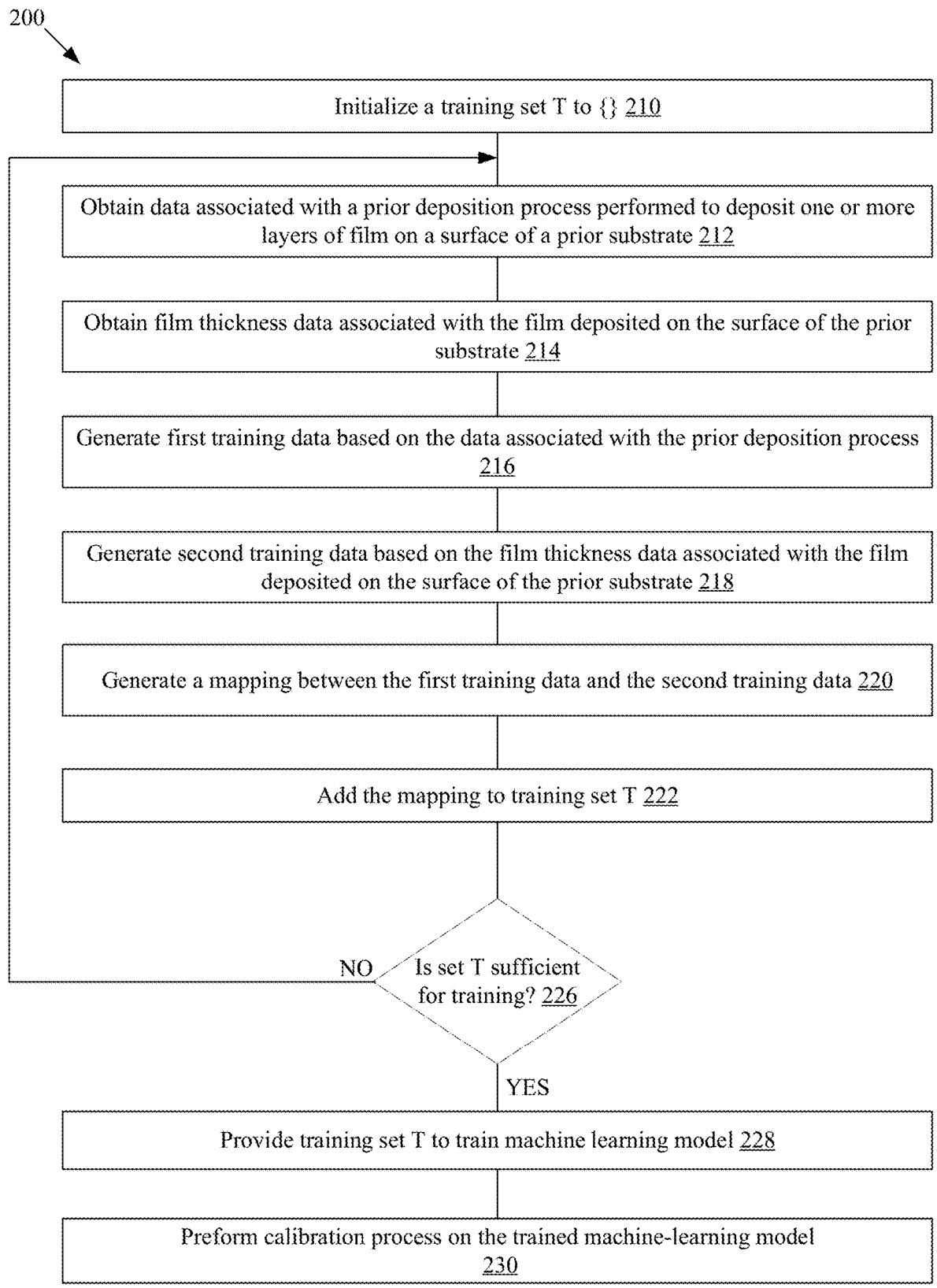
FIG. 2 is a flow diagram of a method for training a machine-learning model, according to certain embodiments.

FIG. 2 is a flow chart of a method 200 for training a machine-learning model, according to aspects of the present disclosure. Method 200 is performed by processing logic that can include hardware (circuitry, dedicated logic, etc.), software (such as is run on a general purpose computer system or a dedicated machine), firmware, or some combination thereof. In one implementation, method 200 can be performed by a computer system, such as computer system architecture 100 of FIG. 1. In other or similar implementations, one or more operations of method 200 can be performed by one or more other machines not depicted in the figures. In some aspects, one or more operations of method 200 can be performed by server machine 170, server machine 180, and/or predictive server 112.

For simplicity of explanation, the methods are depicted and described as a series of acts. However, acts in accordance with this disclosure can occur in various orders and/or concurrently, and with other acts not presented and described herein. Furthermore, not all illustrated acts can be performed to implement the methods in accordance with the disclosed subject matter. In addition, those skilled in the art will understand and appreciate that the methods could alternatively be represented as a series of interrelated states via a state diagram or events. Additionally, it should be appreciated that the methods disclosed in this specification are capable of being stored on an article of manufacture to facilitate transporting and transferring such methods to computing devices. The term article of manufacture, as used herein, is intended to encompass a computer program accessible from any computer-readable device or storage media.

At block 210, processing logic initializes a training set T to an empty set (e.g., { }). At block 212, processing logic obtains sensor data (e.g., sensor values, features, trace data) associated with a prior deposition process performed to deposit one or more layers of film on a surface of a prior substrate. In some embodiments, the sensor data associated with the deposition process is historical data associated with one or more prior deposition settings for a prior deposition process previously performed for a prior substrate at a manufacturing system. For example, the historical data can be historical contextual data associated with the prior deposition process stored at data store 140. In some embodiments, the one or more prior deposition settings can include at least one of a prior temperature setting for the prior deposition process, a prior pressure setting for the prior deposition setting, a prior flow rate setting for a precursor for one or more material of the prior film deposited on the surface of the prior substrate, or any other setting associated with the deposition process. A flow rate setting can refer to a flow rate setting for the precursor at an initial instance of the prior deposition process (referred to as an initial flow rate setting), a flow rate setting for the precursor at a final instance of the prior deposition process (referred to as a final flow rate setting), or a ramping rate for the flow rate of the precursor during the deposition process. In one example, the precursor for the prior film can include a boron-containing precursor or a silicon-containing precursor.

At block 214, processing logic obtains film thickness data associated with the film deposited on the surface of the prior substrate. As discussed previously, film thickness data refers to a thickness measurement of individual film layer(s), total film stack(s), and/or aggregated layer stack(s). Film thickness data can include historical film thickness data for a prior film deposited on a surface of a prior substrate. In some embodiments, the historical film thickness data for the prior film can correspond to a historical metrology measurement value associated with the prior film. Processing logic can obtain the film thickness data associated with the deposited film from data store 140, in accordance with previously described embodiments.

At block 216, processing logic generates first training data based on the obtained data associated with the prior deposition process performed for the prior substrate. At block 218, processing logic generates second training data based on the film thickness data associated with the film deposited on the surface of the prior substrate. For example, the second training data can be associated with a thickness measurement(s) of a film layer(s), a total film stack, and/or an aggregated layer stack. At block 220, processing logic generates a mapping between the first training data and the second training data. The mapping refers to the first training data that includes or is based on data for the prior deposition process performed for the prior substrate and the second training data that includes or is based on film thickness data associated with the film deposited on the surface of the prior substrate, where the first training data is associated with (or mapped to) the second training data. At block 224, processing logic adds the mapping to the training set T.

At block 226, processing logic determines whether the training set, T, includes a sufficient amount of training data to train a machine-learning model. It should be noted that in some implementations, the sufficiency of training set T can be determined based simply on the number of mappings in the training set, while in some other implementations, the sufficiency of training set T can be determined based on one or more other criteria (e.g., a measure of diversity of the training examples, etc.) in addition to, or instead of, the number of input/output mappings. Responsive to determining the training set does not include a sufficient amount of training data to train the machine-learning model, method 200 returns to block 212. Responsive to determining the training set, T, includes a sufficient amount of training data to train the machine-learning model, method 200 continues to block 228.

At block 228, processing logic provides the training set T to train the machine-learning model. In one implementation, the training set T is provided to training engine 182 of server machine 180 to perform the training. In the case of a neural network, for example, input values of a given input/output mapping are input to the neural network, and output values of the input/output mapping are stored in the output nodes of the neural network. The connection weights in the neural network are then adjusted in accordance with a learning algorithm (e.g., backpropagation, etc.), and the procedure is repeated for the other input/output mappings in the training set T.

In some embodiments, method 200 can be used to train multiple machine-learning models for predicting the thickness of layers of different types of material from the same film stack. For example, method 200 can be used to train a first machine-learning model (hereafter "oxide model) for predicting the thickness of oxide layers in an ONON stack, and a second machine-learning model (hereafter "nitride model") for predicting the thickness of nitride layers in the ONON stack. The machine-learning models can then be used to predict, for a deposition process performed for a current substrate, the thickness of each alternating film layer deposited on a surface of the current substrate.

At block 230, processing logic perform a calibration process on the trained machine-learning model. In some embodiments, the processing logic can compare the predictive metrology data to actual (measured) metrology data, and adjust the trained machine-learning model based on the differences in values between the predictive metrology data and the actual metrology data. In one example, the processing logic can compare the predictive thickness data generated by the oxide model to the measured thickness of the aggregated oxide stack. Based on the difference in thickness values, the processing logic can further train or refine the machine-learning model. In another example, the processing logic can compare predictive mass data of the oxide layers, determined from the predictive thickness data generated by the oxide model, to the measured mass of the aggregated oxide stack. Based on the difference in mass values, the processing logic can further train or refine the machine-learning model. In other examples, the processing logic can compare any predictive metrology data to any actual metrology data to further train or refine the trained machine-learning model.

After block 230, machine-learning model 190 can be used to predict, for a deposition process performed for a current substrate, the thickness of one or more layers deposited on a surface of the current substrate. In some embodiments, the predictive component 114 and/or the corrective action component 112 can adjust one or more parameters of a deposition process recipe (e.g., a temperature setting for the process chamber, a pressure setting for the process chamber, a flow rate setting for a precursor for a material included in the film deposited on the substrate surface, etc.) based on a desired target thickness for the a film layer(s). In some embodiments, the deposition process recipe can be adjusted before, during (e.g., in real time) or after the deposition process.

Figure 3:
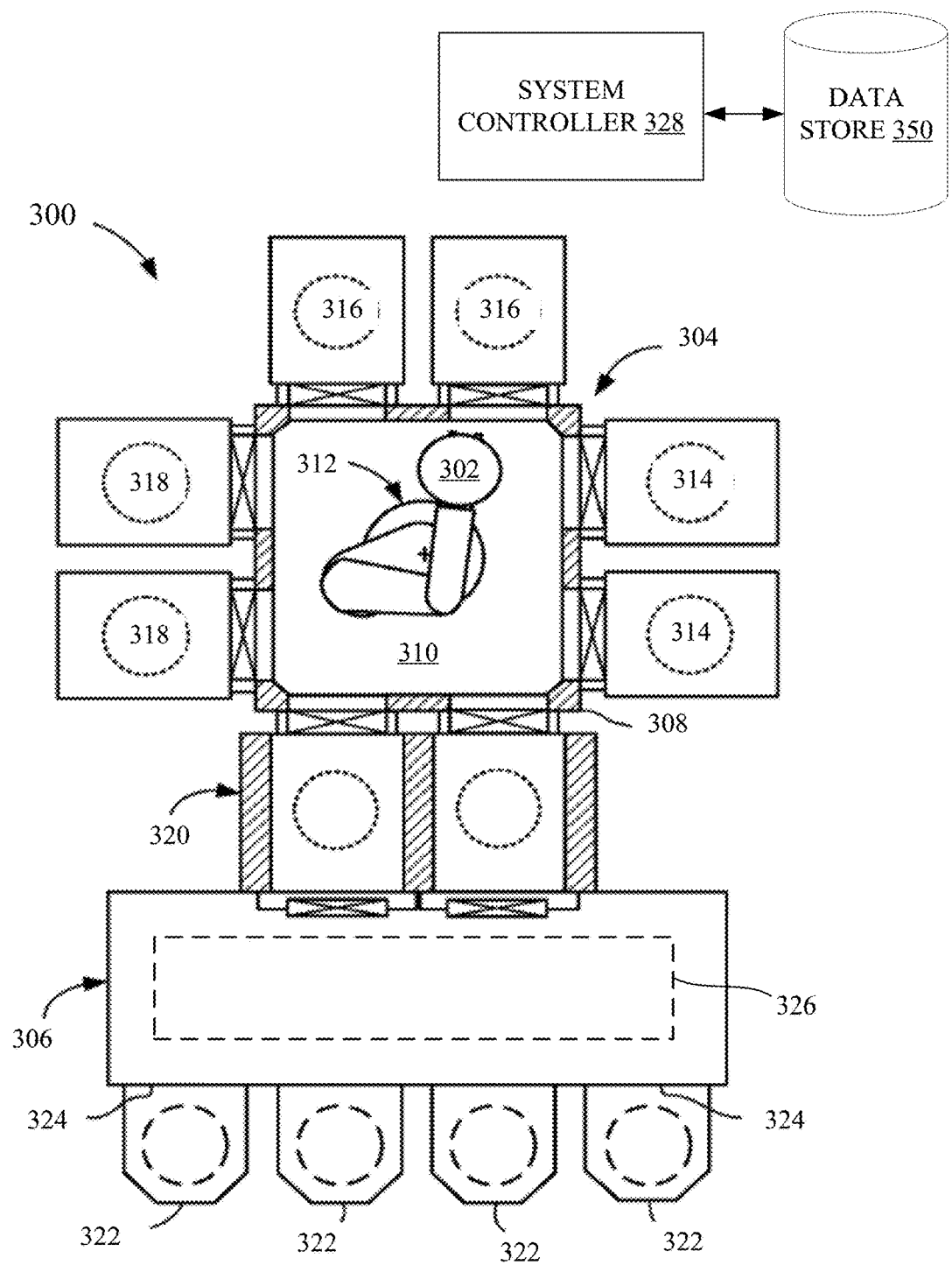
FIG. 3 is a top schematic view of an example manufacturing system, according to certain embodiments.

In some embodiments, a manufacturing system can include more than one process chambers. For example, example manufacturing system 300 of FIG. 3 illustrates multiple process chambers 314, 316, 318. It should be noted that, in some embodiments, data obtained to train the machine-learning model and data collected to be provided as input to the machine-learning model can be associated with the same process chamber of the manufacturing system. In other or similar embodiments, data obtained to train the machine-learning model and data collected to be provided as input to the machine-learning model can be associated with different process chambers of the manufacturing system. In other or similar embodiments, data obtained to train the machine-learning model can be associated with a process chamber of a first manufacturing system and data collected to be provide as input to the machine-learning model can be associated with a process chamber of a second manufacturing system.

FIG. 3 is a top schematic view of an example manufacturing system 300, according to aspects of the present disclosure. Manufacturing system 300 can perform one or more processes on a substrate 302. Substrate 302 can be any suitably rigid, fixed-dimension, planar article, such as, e.g., a silicon-containing disc or wafer, a patterned wafer, a glass plate, or the like, suitable for fabricating electronic devices or circuit components thereon.

Manufacturing system 300 can include a process tool 304 and a factory interface 306 coupled to process tool 304. Process tool 304 can include a housing 308 having a transfer chamber 310 therein. Transfer chamber 310 can include one or more process chambers (also referred to as processing chambers) 314, 316, 318 disposed therearound and coupled thereto. Process chambers 314, 316, 318 can be coupled to transfer chamber 310 through respective ports, such as slit valves or the like. Transfer chamber 310 can also include a transfer chamber robot 312 configured to transfer substrate 302 between process chambers 314, 316, 318, load lock 320, etc. Transfer chamber robot 312 can include one or multiple arms where each arm includes one or more end effectors at the end of each arm. The end effector can be configured to handle particular objects, such as wafers.

Process chambers 314, 316, 318 can be adapted to carry out any number of processes on substrates 302. A same or different substrate process can take place in each processing chamber 314, 316, 318. A substrate process can include atomic layer deposition (ALD), physical vapor deposition (PVD), chemical vapor deposition (CVD), etching, annealing, curing, pre-cleaning, metal or metal oxide removal, or the like. Other processes can be carried out on substrates therein. Process chambers 314, 316, 318 can each include one or more sensors configured to capture data for substrate 302 before, after, or during a substrate process. For example, the one or more sensors can be configured to capture spectral data and/or non-spectral data for a portion of substrate 302 during a substrate process. In other or similar embodiments, the one or more sensors can be configured to capture data associated with the environment within process chamber 314, 316, 318 before, after, or during the substrate process. For example, the one or more sensors can be configured to capture data associated with a temperature, a pressure, a gas concentration, etc. of the environment within process chamber 314, 316, 318 during the substrate process.

A load lock 320 can also be coupled to housing 308 and transfer chamber 310. Load lock 320 can be configured to interface with, and be coupled to, transfer chamber 310 on one side and factory interface 306. Load lock 320 can have an environmentally-controlled atmosphere that can be changed from a vacuum environment (wherein substrates can be transferred to and from transfer chamber 310) to an at or near atmospheric-pressure inert-gas environment (wherein substrates can be transferred to and from factory interface 306) in some embodiments. Factory interface 306 can be any suitable enclosure, such as, e.g., an Equipment Front End Module (EFEM). Factory interface 306 can be configured to receive substrates 302 from substrate carriers 322 (e.g., Front Opening Unified Pods (FOUPs)) docked at various load ports 324 of factory interface 306. A factory interface robot 326 (shown dotted) can be configured to transfer substrates 302 between carriers (also referred to as containers) 322 and load lock 320. Carriers 322 can be a substrate storage carrier or a replacement part storage carrier.

Manufacturing system 300 can also be connected to a client device (not shown) that is configured to provide information regarding manufacturing system 300 to a user (e.g., an operator). In some embodiments, the client device can provide information to a user of manufacturing system 300 via one or more graphical user interfaces (GUIs). For example, the client device can provide information regarding a target thickness profile for a film to be deposited on a surface of a substrate 302 during a deposition process performed at a process chamber 314, 316, 318 via a GUI. The client device can also provide information regarding a modification to a process recipe in view of a respective set of deposition settings predicted to correspond to the target profile, in accordance with embodiments described herein.

Manufacturing system 300 can also include a system controller 328. System controller 328 can be and/or include a computing device such as a personal computer, a server computer, a programmable logic controller (PLC), a microcontroller, and so on. System controller 328 can include one or more processing devices, which can be general-purpose processing devices such as a microprocessor, central processing unit, or the like. More particularly, the processing device can be a complex instruction set computing (CISC) microprocessor, reduced instruction set computing (RISC) microprocessor, very long instruction word (VLIW) microprocessor, or a processor implementing other instruction sets or processors implementing a combination of instruction sets. The processing device can also be one or more special-purpose processing devices such as an application specific integrated circuit (ASIC), a field programmable gate array (FPGA), a digital signal processor (DSP), network processor, or the like. System controller 328 can include a data storage device (e.g., one or more disk drives and/or solid state drives), a main memory, a static memory, a network interface, and/or other components. System controller 328 can execute instructions to perform any one or more of the methodologies and/or embodiments described herein. In some embodiments, system controller 328 can execute instructions to perform one or more operations at manufacturing system 300 in accordance with a process recipe. The instructions can be stored on a computer readable storage medium, which can include the main memory, static memory, secondary storage and/or processing device (during execution of the instructions).

System controller 328 can receive data from sensors included on or within various portions of manufacturing system 300 (e.g., processing chambers 314, 316, 318, transfer chamber 310, load lock 320, etc.). In some embodiments, data received by the system controller 328 can include spectral data and/or non-spectral data for a portion of substrate 302. In other or similar embodiments, data received by the system controller 328 can include data associated with processing substrate 302 at processing chamber 314, 316, 318, as described previously. For purposes of the present description, system controller 328 is described as receiving data from sensors included within process chambers 314, 316, 318. However, system controller 328 can receive data from any portion of manufacturing system 300 and can use data received from the portion in accordance with embodiments described herein. In an illustrative example, system controller 328 can receive data from one or more sensors for process chamber 314, 316, 318 before, after, or during a substrate process at the process chamber 314, 316, 318. Data received from sensors of the various portions of manufacturing system 300 can be stored in a data store 350. Data store 350 can be included as a component within system controller 328 or can be a separate component from system controller 328. In some embodiments, data store 350 can be data store 140 described with respect to FIG. 1.

Figure 4:
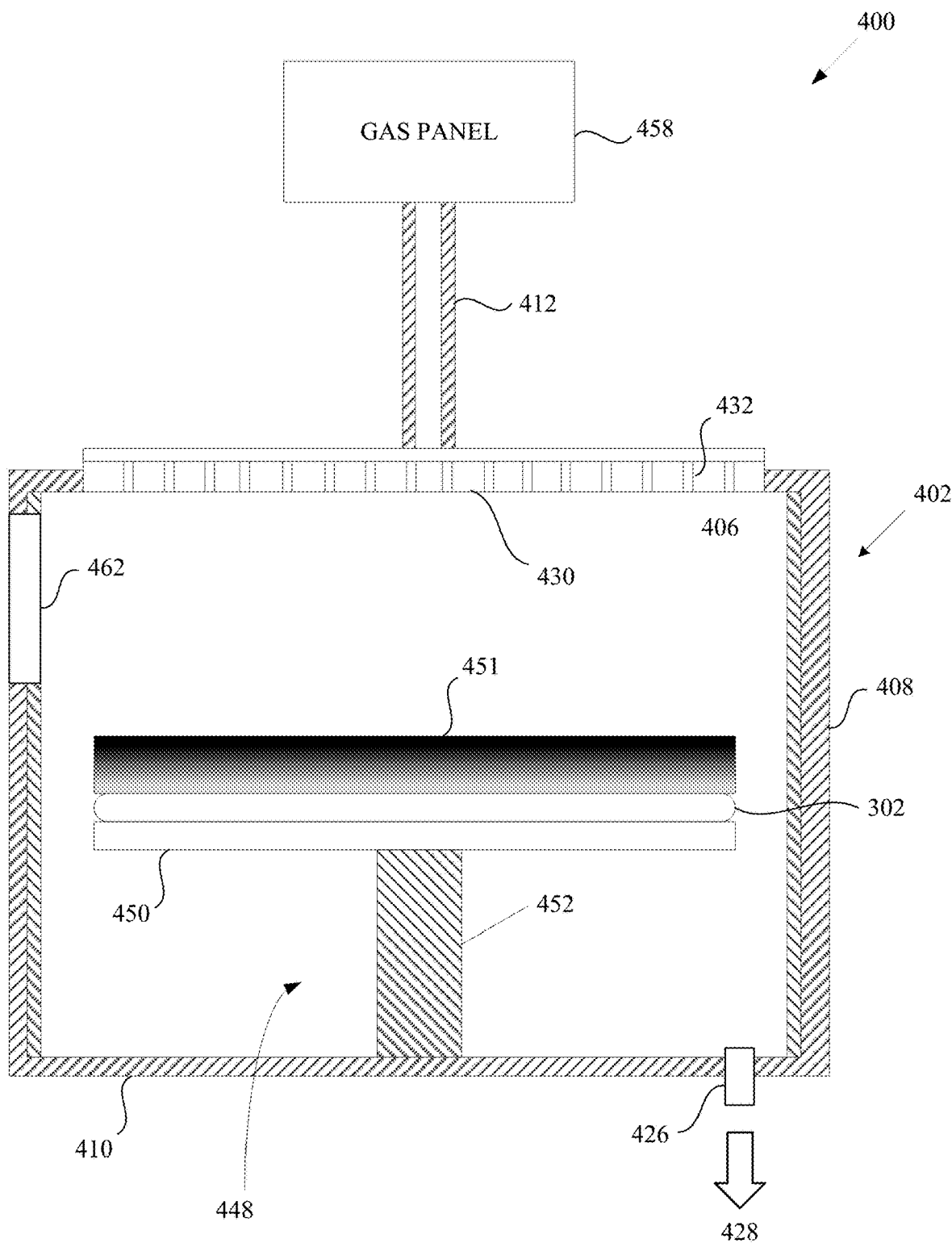
FIG. 4 is a cross-sectional schematic side view of an example process chamber of the example manufacturing system, according to certain embodiments.

FIG. 4 is a cross-sectional schematic side view of a process chamber 400, in accordance with embodiments of the present disclosure. In some embodiments, process chamber 400 can correspond to process chamber 314, 316, 318, described with respect to FIG. 3. Process chamber 400 can be used for processes in which a corrosive plasma environment is provided. For example, the process chamber 400 can be a chamber for a plasma etcher or plasma etch reactor, and so forth. In another example, process chamber can be a chamber for a deposition process, as previously described. In one embodiment, the process chamber 400 includes a chamber body 402 and a showerhead 430 that encloses an interior volume 406. The showerhead 430 can include a showerhead base and a showerhead gas distribution plate. Alternatively, the showerhead 430 can be replaced by a lid and a nozzle in some embodiments, or by multiple pie shaped showerhead compartments and plasma generation units in other embodiments. The chamber body 402 can be fabricated from aluminum, stainless steel or other suitable material such as titanium (Ti). The chamber body 402 generally includes sidewalls 408 and a bottom 410. An exhaust port 426 can be defined in the chamber body 402, and can couple the interior volume 406 to a pump system 428. The pump system 428 can include one or more pumps and throttle valves utilized to evacuate and regulate the pressure of the interior volume 406 of the process chamber 400.

The showerhead 430 can be supported on the sidewall 408 of the chamber body 402. The showerhead 420 (or lid) can be opened to allow access to the interior volume 406 of the process chamber 400, and can provide a seal for the process chamber 400 while closed. A gas panel 458 can be coupled to the process chamber 400 to provide process and/or cleaning gases to the interior volume 406 through the showerhead 430 or lid and nozzle (e.g., through apertures of the showerhead or lid and nozzle). For example. gas panel 458 can provide precursors for materials of a film 451 deposited on a surface of a substrate 302. In some embodiments, a precursor can include a silicon-based precursor or a boron-based precursor. The showerhead 430 can include a gas distribution plate (GDP) and can have multiple gas delivery holes 432 (also referred to as channels) throughout the GDP. A substrate support assembly 448 is disposed in the interior volume 406 of the process chamber 400 below the showerhead 430. The substrate support assembly 448 holds a substrate 302 during processing (e.g., during a deposition process).

In some embodiments, processing chamber 400 can include metrology equipment (not shown) configured to generate in-situ metrology measurements during a process performed at process chamber 400. The metrology equipment can be operatively coupled to the system controller (e.g., system controller 328, as previously described). In some embodiments, the metrology equipment can be configured to generate a metrology measurement value (e.g., a thickness) for film 451 during particular instances of the deposition process. The system controller can generate a thickness profile for film 451 based on the received metrology measurement values from the metrology equipment. In other or similar embodiments, processing chamber 400 does not include metrology equipment. In such embodiments, the system controller can receive one or more metrology measurement values for film 451 after completion of the deposition process at process chamber 400. System controller can determine a deposition rate based on the one or more metrology measurement values and can associate generate the thickness profile for film 451 based on the determined concentration gradient and the determined deposition rate of the deposition process.

Figure 5:
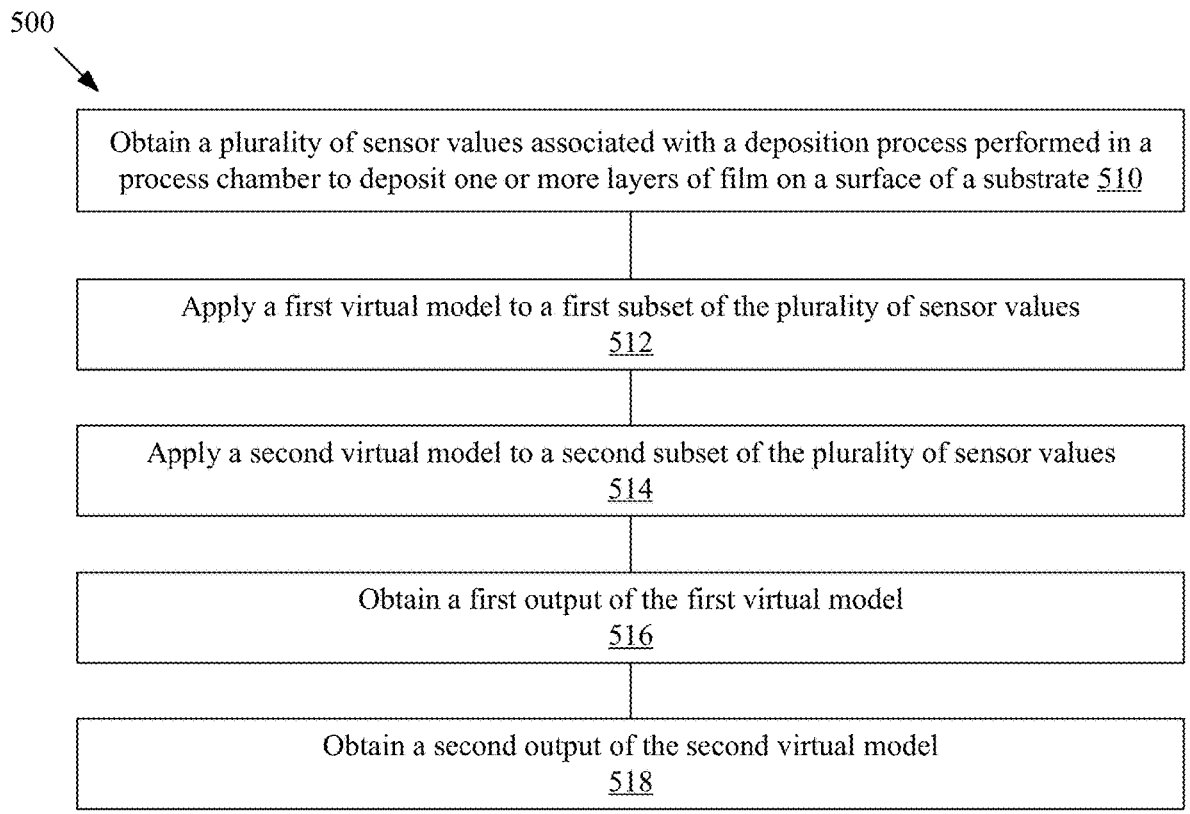
FIG. 5 is a flow diagram of a method for identifying predictive metrology data for layers of a film using a machine-learning model, according to certain embodiments.

FIG. 5 is a flow chart of a method 500 for identifying predictive metrology data for layers of a film using a machine-learning model, according to aspects of the present disclosure. Method 500 is performed by processing logic that can include hardware (circuitry, dedicated logic, etc.), software (such as is run on a general purpose computer system or a dedicated machine), firmware, or some combination thereof. In one implementation, method 500 can be performed by a computer system, such as computer system architecture 100 of FIG. 1. In other or similar implementations, one or more operations of method 500 can be performed by one or more other machines not depicted in the figures. In some aspects, one or more operations of method 500 can be performed by server machine 170, server machine 180, and/or predictive server 112.

At block 510, processing logic obtains a plurality of sensor values associated with a deposition process performed in a process chamber to deposit one or more layers of film on a surface of a substrate. At block 512, processing logic applies a first machine-learning model to a first subset of the plurality of sensor values associated with layers of a first material. At block 514, processing logic applies a second machine-learning model to a second subset of the plurality of sensor values associated with layers of a second material. In some embodiments, the first and second machine-learning models are trained based on historical sensor data and historical metrology data.

At block 516, processing logic obtains a first output of the first machine-learning model. For example, the first output can identify first predictive metrology data for one or more layers of the first material of the film (e.g., oxide).

At block 518, processing logic obtains a second output of the second machine-learning model. For example, the second output can identify second predictive metrology data for one or more layers of the second material of the film (e.g., nitride). In some embodiments, the predictive metrology data includes a contour map having a set of spatial measurements, each spatial measurement indicating a thickness of a particular location of a plurality of locations on one or more layers on the substrate. In some embodiments, the predictive metrology data indicates an average predictive layer thickness.

Figure 6:
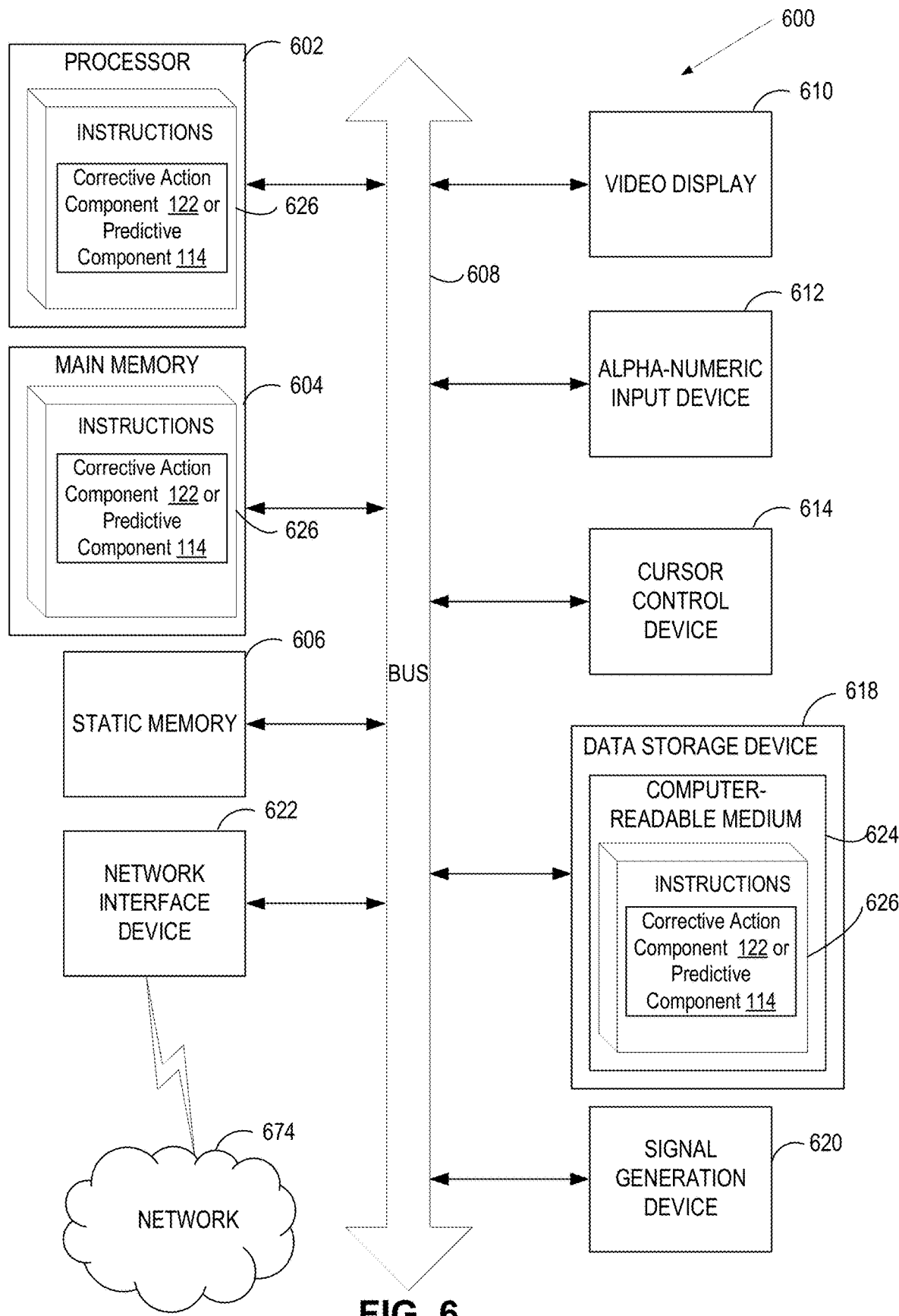
FIG. 6 is a block diagram illustrating a computer system, according to certain embodiments.

FIG. 6 is a block diagram illustrating a computer system 600, according to certain embodiments. In some embodiments, computer system 600 may be connected (e.g., via a network, such as a Local Area Network (LAN), an intranet, an extranet, or the Internet) to other computer systems. Computer system 600 may operate in the capacity of a server or a client computer in a client-server environment, or as a peer computer in a peer-to-peer or distributed network environment. Computer system 600 may be provided by a personal computer (PC), a tablet PC, a Set-Top Box (STB), a Personal Digital Assistant (PDA), a cellular telephone, a web appliance, a server, a network router, switch or bridge, or any device capable of executing a set of instructions (sequential or otherwise) that specify actions to be taken by that device. Further, the term "computer" shall include any collection of computers that individually or jointly execute a set (or multiple sets) of instructions to perform any one or more of the methods described herein.

In a further aspect, the computer system 600 may include a processing device 602, a volatile memory 604 (e.g., Random Access Memory (RAM)), a non-volatile memory 606 (e.g., Read-Only Memory (ROM) or Electrically-Erasable Programmable ROM (EEPROM)), and a data storage device 616, which may communicate with each other via a bus 608.

Processing device 602 may be provided by one or more processors such as a general purpose processor (such as, for example, a Complex Instruction Set Computing (CISC) microprocessor, a Reduced Instruction Set Computing (RISC) microprocessor, a Very Long Instruction Word (VLIW) microprocessor, a microprocessor implementing other types of instruction sets, or a microprocessor implementing a combination of types of instruction sets) or a specialized processor (such as, for example, an Application Specific Integrated Circuit (ASIC), a Field Programmable Gate Array (FPGA), a Digital Signal Processor (DSP), or a network processor).

Computer system 600 may further include a network interface device 622 (e.g., coupled to network 674). Computer system 600 also may include a video display unit 610 (e.g., an LCD), an alphanumeric input device 612 (e.g., a keyboard), a cursor control device 614 (e.g., a mouse), and a signal generation device 620.

In some implementations, data storage device 616 may include a non-transitory computer-readable storage medium 624 on which may store instructions 626 encoding any one or more of the methods or functions described herein, including instructions encoding components of FIG. 1 (e.g., corrective action component 122, predictive component 114, etc.) and for implementing methods described herein.

Instructions 626 may also reside, completely or partially, within volatile memory 604 and/or within processing device 602 during execution thereof by computer system 600, hence, volatile memory 604 and processing device 602 may also constitute machine-readable storage media.

While computer-readable storage medium 624 is shown in the illustrative examples as a single medium, the term "computer-readable storage medium" shall include a single medium or multiple media (e.g., a centralized or distributed database, and/or associated caches and servers) that store the one or more sets of executable instructions. The term "computer-readable storage medium" shall also include any tangible medium that is capable of storing or encoding a set of instructions for execution by a computer that cause the computer to perform any one or more of the methods described herein. The term "computer-readable storage medium" shall include, but not be limited to, solid-state memories, optical media, and magnetic media.

The methods, components, and features described herein may be implemented by discrete hardware components or may be integrated in the functionality of other hardware components such as ASICS, FPGAs, DSPs or similar devices. In addition, the methods, components, and features may be implemented by firmware modules or functional circuitry within hardware devices. Further, the methods, components, and features may be implemented in any combination of hardware devices and computer program components, or in computer programs.

Unless specifically stated otherwise, terms such as "receiving," "performing," "providing," "obtaining," "causing," "accessing," "determining," "adding," "using," "training," or the like, refer to actions and processes performed or implemented by computer systems that manipulates and transforms data represented as physical (electronic) quantities within the computer system registers and memories into other data similarly represented as physical quantities within the computer system memories or registers or other such information storage, transmission or display devices. Also, the terms "first," "second," "third," "fourth," etc. as used herein are meant as labels to distinguish among different elements and may not have an ordinal meaning according to their numerical designation.

Examples described herein also relate to an apparatus for performing the methods described herein. This apparatus may be specially constructed for performing the methods described herein, or it may include a general purpose computer system selectively programmed by a computer program stored in the computer system. Such a computer program may be stored in a computer-readable tangible storage medium.

The methods and illustrative examples described herein are not inherently related to any particular computer or other apparatus. Various general purpose systems may be used in accordance with the teachings described herein, or it may prove convenient to construct more specialized apparatus to perform methods described herein and/or each of their individual functions, routines, subroutines, or operations. Examples of the structure for a variety of these systems are set forth in the description above.

The above description is intended to be illustrative, and not restrictive. Although the present disclosure has been described with references to specific illustrative examples and implementations, it will be recognized that the present disclosure is not limited to the examples and implementations described. The scope of the disclosure should be determined with reference to the following claims, along with the full scope of equivalents to which the claims are entitled.

The invention claimed is:

1. A method comprising:
obtaining, by a processor, sensor data associated with a deposition process performed in a process chamber to deposit a film stack on a surface of a substrate, wherein the film stack comprises a plurality of layers of a first material and a plurality of layers of a second material;
obtaining metrology data associated with the film stack;
training a first machine-learning model based on the sensor data and the metrology data, wherein the first machine-learning model is trained to generate predictive metrology data associated with layers of the first material; and
training a second machine-learning model based on the sensor data and the metrology data, wherein the second machine-learning model is trained to generate predictive metrology data associated with layers of the second material.

2. The method of claim 1, further comprising:
updating the first machine-learning model and the second machine learning model based on a comparison between the predictive metrology data and measured metrology data.

3. The method of claim 2, wherein the predictive metrology data comprise predictive mass data and the measured metrology data comprises measured mass data.

4. The method of claim 1, wherein the metrology data comprises a measured thickness of an aggregated stack of a single material.

5. The method of claim 1, wherein the metrology data comprises thickness data obtained from a Transmission Electron Microscope (TEM) analysis.

6. The method of claim 1, wherein the metrology data comprises a measured thickness of the film stack.

7. The method of claim 1, wherein the first material comprises oxide and the second material comprises nitride.

8. The method of claim 1, further comprising:
determining, using the first machine-learning model and the second machine-learning model, predictive metrology data for a current substrate undergoing a current deposition process.

9. The method of claim 8, further comprising:
adjusting a deposition process recipe associated with the current deposition process based on the predictive metrology data.

10. A system comprising:
a memory; and
a processing device, coupled to the memory, to:
obtain sensor data associated with a deposition process performed in a process chamber to deposit a film stack on a surface of a substrate, wherein the film stack comprises a plurality of layers of a first material and a plurality of layers of a second material;
obtain metrology data associated with the film stack;
train a first machine-learning model based on the sensor data and the metrology data, wherein the first machine-learning model is trained to generate predictive metrology data associated with layers of the first material; and
train a second machine-learning model based on the sensor data and the metrology data, wherein the second machine-learning model is trained to generate predictive metrology data associated with layers of the second material.

11. The system of claim 10, wherein the processing device is further to:
update the first machine-learning model and the second machine-learning model based on a comparison between the predictive metrology data and measured metrology data.

12. The system of claim 11, wherein the predictive metrology data comprise predictive mass data and the measured metrology data comprises measured mass data.

13. The system of claim 10, wherein the metrology data comprises a measured thickness of an aggregated stack of a single material.

14. The system of claim 10, wherein the metrology data comprises thickness data obtained from a Transmission Electron Microscope (TEM) analysis.

15. The system of claim 10, wherein the metrology data comprises a measured thickness of the film stack.

16. The system of claim 10, wherein the first material comprises oxide and the second material comprises nitride.

17. The system of claim 10, wherein the processing device is further to:
determine, using the first machine-learning model and the second machine-learning model, predictive metrology data for a current substrate undergoing a current deposition process.

18. The system of claim 17, wherein the processing device is further to:
adjust a deposition process recipe associated with the current deposition process based on the predictive metrology data.

19. A non-transitory machine-readable storage medium storing instructions which, when executed cause a processing device to perform operations comprising:
obtaining, by a processor, sensor data associated with a deposition process performed in a process chamber to deposit a film stack on a surface of a substrate, wherein the film stack comprises a plurality of layers of a first material and a plurality of layers of a second material;
obtaining metrology data associated with the film stack;
training a first machine-learning model based on the sensor data and the metrology data, wherein the first machine-learning model is trained to generate predictive metrology data associated with layers of the first material; and
training a second machine-learning model based on the sensor data and the metrology data, wherein the second machine-learning model is trained to generate predictive metrology data associated with layers of the second material.

20. A method comprising:
obtaining a plurality of sensor values associated with a deposition process performed in a process chamber to deposit layers of film on a surface of a substrate;
applying a first machine-learning model to a first subset of the plurality of sensor values, the first machine-learning model trained based on historical sensor data and metrology data associated with layers of a first material;
applying a second machine-learning model to a second subset of the plurality of sensor values, the second machine-learning model trained based on the historical sensor data and metrology data associated with layers of a second material;
obtaining a first output of the first machine-learning model, the first output indicating first predictive metrology data for layers of the first material of the film; and
obtaining a second output of the second machine-learning model, the second output indicating second predictive metrology data for layers of the second material of the film.

* * * * *